United States Patent [19]

Bryant et al.

[11] Patent Number: 5,114,465

[45] Date of Patent: * May 19, 1992

[54] SUBSTITUTED PYRIDINE COMPOUNDS AND HERBICIDAL COMPOSITIONS AND METHODS

[75] Inventors: Robert D. Bryant, St. Louis; Shridhar G. Hegde, Maryland Heights; Len F. Lee, St. Charles, all of Mo.

[73] Assignee: Monsanto Company, St. Louis, Mo.

[ * ] Notice: The portion of the term of this patent subsequent to Dec. 5, 2006 has been disclaimed.

[21] Appl. No.: 716,418

[22] Filed: Jun. 17, 1991

Related U.S. Application Data

[63] Continuation-in-part of Ser. No. 457,893, Dec. 27, 1989, abandoned.

[51] Int. Cl.⁵ .................. A01N 43/40; C07D 213/75

[52] U.S. Cl. ...................... 71/94; 546/261; 546/296; 546/288; 546/298; 546/299

[58] Field of Search ............. 71/94; 546/261, 296, 546/288, 298, 299

[56] References Cited

U.S. PATENT DOCUMENTS

| | | | |
|---|---|---|---|
| 4,609,399 | 9/1986 | Lee | 71/94 |
| 4,692,184 | 9/1987 | Lee | 71/94 |
| 4,885,026 | 12/1989 | Lee et al. | 71/94 |

Primary Examiner—Mary C. Lee
Assistant Examiner—Jacqueline Haley
Attorney, Agent, or Firm—Grace L. Bonner; James C. Bolding; Howard C. Stanley

[57] ABSTRACT 2- or 6-fluoromethyl-3-pyridinecarboxylate derivatives with 5-(haloalkyl) carboxamide or 5-(haloalkyl)carbamate substitution, useful as herbicides and herbicide intermediates.

12 Claims, No Drawings

SUBSTITUTED PYRIDINE COMPOUNDS AND HERBICIDAL COMPOSITIONS AND METHODS

This is a continuation-in-part of co-pending application Ser. No. 07/457,893, filed Dec. 27, 1989, now abandoned.

FIELD OF THE INVENTION

This invention relates to a new class of 2,6-substituted pyridine derivatives having activity as herbicides and as intermediates in the preparation of other herbicidal compounds, to their use as herbicides, and to herbicidal compositions containing them.

BACKGROUND OF THE INVENTION

Pyridine derivatives have, for many years, been investigated for use in the biological sciences. Pyridine dicarboxylate compounds useful as herbicides are described in U.S. Pat. No. 4,692,184. These compounds have fluorinated methyl groups at the 2- and 6-positions and carboxylic acids or their derivatives at the 3- and 5-positions and are characterized further by a 4-position substituent in which the atom attached to the pyridine ring is a carbon atom, such as alkyl, alkoxyalkyl, alkylthioalkyl, aralkyl, and like moieties.

More relevant compounds include those which contain fluorinated methyl groups at the 2- and 6-positions, carboxylic acids or their derivatives at the 3- and/or 5-positions and at the 4-position have a substituent group beginning with a hetero atom selected from O, S, N and P. These compounds are likewise useful as herbicides.

Other herbicidal pyridines are those of U.S. Pat. No. 4,609,399 which have a fluorinated methyl group at the 2-position, a carboxylic acid group or derivative thereof at the 3- and/or 5-position, and alkoxy groups at the 4- and 6-positions.

More relevant to the compounds of this invention are those disclosed in U.S. Pat. No. 4,885,026, which are 5-amino pyridine 3-carboxylate derivatives.

BRIEF DESCRIPTION OF THE INVENTION

It is an object of this invention to provide novel pyridine compounds, as well as herbicidal methods and compositions utilizing such compounds.

The novel compounds of this invention are useful as herbicides or intermediates which can be converted to herbicides and are represented by the generic formula

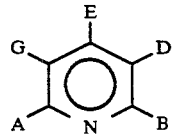

wherein:
one of A and B is selected from the group consisting of fluorinated methyl and chlorofluorinated methyl radicals, and the other is selected from the group consisting of fluorinated methyl, chlorofluorinated methyl and alkyl radicals;

E is selected from the group consisting of alkyl, alkenyl, cycloalkyl, cycloalkylalkyl, haloalkyl, and alkylthioalkyl radicals;

G is selected from the group consisting of hydroxycarbonyl, alkoxycarbonyl, haloalkoxycarbonyl, alkylthiocarbonyl, alkenyloxycarbonyl, alkynyloxycarbonyl, cyano, pyridylthiocarbonyl, aminocarbonyl, monoalkylsubstituted aminocarbonyl, and dialkylsubstituted aminocarbonyl, or is the same as D; and D is —NHR in which R is selected from the group consisting of 3-halopropylcarbonyl, 4-halobutylcarbonyl, and 2-haloethoxycarbonyl radicals, optionally substituted with one or more groups selected from alkyl, halo, alkylidene, alkoxy, alkylthio, and haloalkyl radicals.

As used herein throughout the specification and claims, the following terms have the following meanings:

The term "alkyl" means herein both straight and branched chain saturated hydrocarbon radicals having 1 to 7 carbon atoms, unless a different carbon number range is expressly stated. Examples of such radicals include, but are not limited to, ethyl, methyl, n-propyl, 1-ethylpropyl, 1-methylpropyl, 2-methylpropyl, n-butyl, 1,1-dimethylethyl, 2,2-dimethylpropyl, pentyl, isopropyl, and the like.

The term "cycloalkyl" means saturated cyclic radicals having 3 to 7 carbon atoms, such as cyclopropyl, cyclobutyl, cyclopentyl, cyclohexyl, and cycloheptyl.

The terms "alkenyl" and "alkynyl" herein mean alkenyl and alkynyl groups having 2 to 7 carbon atoms. Examples of such alkenyl groups include ethenyl, 1-propenyl, 2-propenyl, 1-butenyl, 2-butenyl, 3-butenyl, 2-methyl-1-propenyl, 2-methyl-2-propenyl, 1-methylethenyl, 4-pentenyl, and the like. Examples of such lower alkynyl groups include ethynyl, 1-propynyl, 2-propynyl, and so forth.

The term "cycloalkylalkyl" is intended to mean alkyl radicals having 1 to 3 carbon atoms which is substituted with a cycloalkyl group having 3 to 7 carbon atoms.

The term "haloalkyl" is intended to mean an alkyl radical (as defined above) substituted with one or more halogen atoms selected from F, Cl, Br, and I. "Haloalkenyl" and "haloalkynyl" refer to alkenyl and alkynyl radicals substituted with one or more halogens.

The term "cation" means any monovalent cation derived from a base which is capable of forming a salt. Typical cations include, but are not limited to, alkali metals such as sodium, potassium, and lithium; alkaline earth metals such as calcium and magnesium; and ammonium salts, organic amines, sulfonium and phosphonium salts, and other salt complexes.

The term "fluorinated methyl" means methyl radicals having one or more fluorine atoms attached thereto, and includes radicals wherein all hydrogen atoms replaced by fluorine.

The term "chlorofluorinated methyl" means herein a methyl radical having at least one hydrogen replaced by fluorine and at least one other hydrogen replaced by chlorine.

The term "halogen" and its combining form "halo" are used herein to refer to fluorine, chlorine, bromine, and iodine.

DETAILED DESCRIPTION OF THE INVENTION

As used throughout the specification, including the Examples, the following abbreviations have the following meanings:
THF - tetrahydrofuran
DBU - 1,8-diazabicyclo-[5.4.0]-undec-5-ene
HPLC - high pressure liquid chromatography
TLC - thin layer chromatography The compounds of the present invention are useful as intermediates in the preparation of pyridine cyclic imidate compounds by cyclization of the haloalkyl carboxamide substituent (D) of the compounds of this invention. The compounds of this invention may be prepared by reaction of a 3- or 5-amino pyridine with a substituted or unsubstituted haloalkyl acid chloride. The 3- or 5-amino pyridine is prepared from a 3- or 5-chlorocarbonyl pyridine.

Aminopyridines and their preparation from the chlorocarbonyl pyridines (or pyridine acid chlorides) are described in more detail in U.S. Patent 4,885,026 and in European Patent Publication 0252055.

Preparation of the chlorocarbonyl pyridines (pyridine acid chlorides) starting compounds is illustrated below in Steps 1-9. Preparation of the amino pyridines is shown below in Examples A-1 to A-7. Preparation of the haloalkylamides of this invention is shown in Examples 1 to 20, while preparation of the haloethoxy carboxamides (or haloethyl carbamates) is shown in Examples 23-25. Preparation of the pyridine cyclic imidate compounds from the compounds of this invention is shown in Examples P-1 to P-22.

PREPARATION OF PYRIDINE ACID CHLORIDE STARTING MATERIALS

The compounds of this invention are prepared using as a starting material a pyridine 3,5-dicarboxylic acid as the mono-ester/mono-chloride or the dichloride. Steps 1-9 which follow set out in detail the preparation of three specific acid halides which are used as starting materials for the compounds of this invention. Other acid halides may be readily prepared using the procedures of Steps 1-9 by varying the ketoester and aldehyde used in Step 1 to obtain the desired substituents in the pyridinedicarboxylate product. Other suitable pyridinecarboxylate acid halides used as starting materials are shown in U.S. Pat. No. 4,692,184 in Examples 44-51 and 82-83 inclusive, the disclosure of which is incorporated by reference herein in its entirety. Other acid halide starting materials may be readily prepared using the techniques set out in that U.S. Patent.

In Step 1, a β-ketoester is reacted with an aldehyde to form a pyran. The pyran is then reacted with ammonia to form a dihydroxypiperidine (Step 2), which is dehydrated to make a dihydropyridine compound (Step 3). The dihydropyridine is then oxidized or dehydrofluorinated to prepare a pyridinedicarboxylate compound (Step 4).

The ester groups of the pyridinedicarboxylate compound are the ester groups of the β-ketoester, and the 4-position of the pyridine is substituted with the same substituent as is on the aldehyde reagent.

When the pyridinedicarboxylate is substituted at the 2- or 6-position with a trifluoromethyl radical and at the other of these positions with a difluoromethyl radical, hydrolysis of the pyridine dicarboxylate compound occurs selectively on the side having the difluoromethyl group when one equivalent of a base such as KOH is employed in the hydrolysis (Step 8). When two equivalents of base or more are employed, the dicarboxylate is hydrolyzed to the diacid (Step 5). The diacid may be converted to the diacid chloride by treatment with a chlorinating agent such as $SOCl_2$ or $PCl_5$. Following this conversion, treatment with one equivalent of an alcohol selectively esterifies the diacid chloride on the chloride group adjacent to the difluoromethyl group.

Step 1

Preparation of dimethyl 2,6-bis(trifluoromethyl)-2,6-dihydroxy-4-(2-methylpropyl)-tetrahydro-3,5-pyrandicarboxylate. To a mechanically stirred mixture of 280 g (2.0 mol) of 80% pure methyl trifluoroacetoacetate and 86 g (1.0 mol) isovaleraldehyde is added 1 mL of piperidine. An exothermic reaction occurs and the temperature of the reaction mixture reaches 105° C. After 5 hours of stirring, the reaction mixture is triturated with 450 ml hexane and 30 mL ether and cooled with a dry ice bath to give 1.68 g of a first crop, m.p. 83°-87° C., and 14.51 g of a second crop, m.p. 67°-73° C.

The first crop is the desired product which contains a mixture of 5:1 cis and trans isomers.

The second crop is a 2:1 mixture of cis and trans isomers. The mother liquor is concentrated to give 344 g of a residue which is a crude mixture of cis and trans isomer of the desired product.

Step 2

Preparation of dimethyl 2,6-bis(trifluoromethyl)-2,6-dihydroxy-4-(2-methylpropyl)-3,5-piperidinedicarboxylate. To a solution of 344 g (0.920 mol) crude product from Step 1 in 500 mL THF is passed 58 g (3.4 mol) of gaseous ammonia for 3 hours. The reaction mixture is concentrated and the residue (332 g) is recrystallized from hexane-ether to give 53.7 g (a 13% yield from methyl trifluoroacetoacetate) of the desired product as a white solid, m.p. 102°-106° C.

The mother liquor is concentrated to provide more of the crude desired product.

Step 3

Preparation of a 2:1 mixture of dimethyl 2,6-bis(trifluoromethyl)-1,4-dihydro-4-(2-methylpropyl)-3,5-pyridinedicarboxylate and its 3,4-dihydropyridine isomer. To an ice water cooled mixture of 200 mL conc. sulfuric acid and 200 mL methylene chloride is added 48.7 g (0.115 mol) of the product of Step 2 in one step. The reaction mixture is stirred for 20 minutes and poured into 1 L of ice water The methylene chloride layer is separated and washed once with 100 mL saturated sodium bicarbonate, dried and concentrated to give 28.0 g (64.6%) of crude product. A portion (5.0 g) of this product is kugelrohr distilled at 0.5 torr (pot temperature at 120° C.) to give 4.8 g of the desired product, $n_d^{25}$ 1.4391.

Step 3 product may be prepared in better overall yield without isolation of Step 1 and Step 2 product by the following procedure:

To a mechanically stirred mixture of 340.3 g (1.98 mol) of 98.9% pure methyl trifluoroacetoacetate (MTFAA), 100 mL toluene, and 0.86 g (0.01 mol) piperidine was added 90.5 g (1.03 mol) isovaleraldehyde in 20 minutes. The reaction mixture was exothermic, causing a rise in temperature to 83° C. The reaction mixture was maintained at 80° C. for 3 hours. $^{19}F$ NMR showed that the reaction was 89% complete. Heat was removed, and the reaction mixture was diluted with 125 mL toluene and stirred overnight (16 hours). Gaseous ammonia was passed through the reaction mixture, resulting in a rise in temperature to 68° C. in 50 minutes. A water cooling bath was applied to the reaction vessel to reduce the reaction temperature to 53° C. while ammonia was passed continuously. A total of 47.3 g (2.78 mol) ammonia was passed through the reaction mixture over 1.5 hours. The reaction mixture was diluted with 100 mL of toluene. A Claisen distillation head was attached to the reaction vessel.

Excess ammonia and part of toluene were removed in vacuo (water aspirator) while the temperature was maintained at 26° C. An additional 200 mL toluene were added, and the distillation was continued to remove a total of 200 mL of distillate in 1.5 hours. The reaction mixture was diluted with 100 mL toluene and cooled to 5° C. with an ice bath. Sulfuric acid (453 g, 4.53 mol) was added in 5 minutes. The exotherm caused the temperature to rise to 25° C. The temperature gradually subsided to 5° C. in 10 minutes and was maintained at 5° C. for 40 minutes. An additional 95 g (0.95 mol) sulfuric acid was added, and the reaction mixture was stirred at 5° C. for 20 minutes before being poured into a mixture of 500 mL toluene and 2 L of ice water. The toluene layer was separated and the aqueous layer was extracted once with 500 mL toluene. The combined toluene extracts were washed successively with 500 mL water, 500 mL saturated aqueous $NaHCO_3$, 500 mL brine and concentrated in vacuo to 363.6 g of an oil. GC area percent analysis indicated that the oil contained 9% of the 3,4-dihydropyridine isomer and 75.4% of the 1,4-dihydropyridine isomer corresponding to an overall yield of 82.9% from MTFAA.

Step 4

Preparation of dimethyl 2-(difluoromethyl)-6-(trifluoromethyl)-4-(2-methylpropyl)-3,5-pyridinedicarboxylate.

(a) Reaction of the Product of Step 3 with DBU

A mixture of 23.0 g (0.0591 mol) of the product of Step 3, 12.2 g (0.077 mol) of 96% pure DBU, and 100 mL THF is held at reflux for 3 days and poured into 250 mL of 3 N HCl. The oil precipitate is extracted into ether (2×100 mL). The ether extracts are dried over magnesium sulfate and concentrated to give 14.4 g of an oil which, according to $^1H$ NMR, contained the desired product and acidic products. This oil is dissolved in ether and extracted with 100 mL saturated sodium bicarbonate. The ether layer is dried over magnesium sulfate and concentrated to give 8.9 g of an oil which is 71% pure desired product (by $^{19}F$ NMR).

The sodium bicarbonate extract is acidified with conc HCl to give an oil which is extracted into ether. The ether layer is dried over magnesium sulfate and concentrated to give 4.8 g of a residue which contained monocarboxylic acid and dicarboxylic acid (9:1) derived from the desired product. This residue is treated with 3.0 g (0.0217 mol) potassium carbonate, 20 mL methyl iodide, and 50 mL acetone. The mixture is held at reflux for 42 hours and concentrated. The residue is treated with water and extracted with ether (2×100 mL). The ether layer is dried and concentrated. The residue is kugelrohr distilled at 1 torr (pot temperature of 130° C.) to give 5.1 g (23.4% from Step 3) of the desired product as an oil, $n_D^{25}$ 1.4478. This product crystallizes after standing, m.p. 36°–37° C.

The 71% pure desired product described previously was chromatographed by HPLC using 3% ethyl acetate/cyclohexane as eluent to give an earlier fraction (0.79 g, retention time 7–8.5 minutes) which was identified as methyl 6-(difluoromethyl)-4-(2-methylpropyl)-2-(trifluoromethyl)-3-pyridinecarboxylate. The second fraction (retention time 8.5–18.5 minutes) is an additional 6.4 g (29.4%) of pure desired product, $n_D^{25}$1.4474.

(b) Reaction of the Product of Step 3 with Tributylamine. A mixture of 38.9 g of an 80% pure product of Step 3 and 20.5 g tributylamine is heated to 155° C. in 30 minutes. The reaction mixture was cooled to 30° C. and diluted with 100 mL toluene. The toluene solution is washed successively with 6 N HCl, saturated sodium bicarbonate, and brine; dried; and concentrated to give 36.4 g of a 73% pure product which corresponds to an 86% yield. This reaction can also be carried out in excess of tributylamine (10 equivalents) giving essentially similar results.

(c) Reaction of the Product of Step 3 with Tributylamine in Toluene. A mixture of 38.9 g of an 80% pure product of Step 3, 20.4 g tributylamine and 30 mL toluene is heated to 115° C. in 40 minutes and held at 115° C. for 1 hour and 40 minutes. The reaction mixture is cooled and worked up as in (b) above to give 36.3 g of a 76% pure product which corresponds to a 90% yield.

(d) Reaction of the Product of Step 3 with Tributylamine. A mixture of 11.8 g of an 80% pure product of Step 3 and 3.34 g triethylamine is heated at 100° C. for 10 minutes, then at 125° C. for 10 minutes. The reaction mixture was cooled and worked up as in (b) above to give 8.14 g of a 76% pure product which corresponds to a 63% yield.

(e) Reaction of the Product of Step 3 with 2,6-Lutidine in the Presence of a Catalytic Amount of DBU. A mixture of 5.0 g of product of Step 3 and 2.13 g 2,6-lutidine is heated at 143° C. for 30 minutes. Two drops of DBU are added and the reaction mixture is heated for additional 1.5 hours, cooled and worked up as in (b) above to give 4.23 g of the desired product. The reaction can also be carried out with an excess of 2,6-lutidine and a catalytic amount of DBU without solvent or in the presence of toluene as a solvent giving similar results.

Step 5

Preparation of 2-(difluoromethyl)-6-(trifluoromethyl)-4-(2-methylpropyl)-3,5-pyridinedicarboxylic acid. A 5-liter flask was charged with 894 g (2.42 mol) of the compound of Step 4 and 1 L water. To this was added a solution of 574 g (8.7 mol) KOH in 800 mL water. The mixture was refluxed overnight, after which HPLC showed that the reaction was complete. The flask was cooled to room temperature, acidified with HCl, and stirred until the organic phase solidified. The solids were filtered, washed with water, and dried in a fluid bed dryer. The diacid was obtained (756 g, 91.6% yield) as a brown solid.

Step 6

Preparation of 3,5-bis-(chlorocarbonyl)-2-(difluoromethyl)-4-(2-methylpropyl)-6-(trifluoromethyl)-pyridine. The diacid product of Step 5 (37.06 g, 0.108 mol) was refluxed with 150 mL $SOCl_2$ for three hours. At this time, $^{19}F$ NMR indicated the reaction was complete. The excess $SOCl_2$ was removed by rotary evaporation, leaving a dark oil which was the bis-acid chloride. This was kugelrohr distilled at 100° C. to give a colorless oil.

Step 7

Preparation of methyl 5-chlorocarbonyl-2-(difluoromethyl)-4-(2-methylpropyl)-6-(trifluoromethyl)-pyridine-3-carboxylate. The product of Step 6 was then dissolved in 100 mL THF followed by 100 mL methanol. After 2½ hours the solvent was evaporated, leaving 31.2 g white solid, m.p. 71°–75° C. in 77% yield.

Step 8

Preparation of 2-(difluoromethyl)-4-(2-methylpropyl)-6-(trifluoromethyl)-3,5-pyridinedicarboxylic acid. 5-methyl ester. A 1-liter 4-necked flask was charged with 300 g of product of Step 4 and about 200 mL ethanol. In a separate flask was combined 59.14 g (0.896 mol) of 85% KOH and about 100 mL water. The aqueous solution was poured into the organics and the flask was equipped with a mechanical stirrer, thermometer, nitrogen inlet and a water cooled condenser. The reaction mixture was heated to reflux, refluxed for 45 minutes, and cooled. The reaction mixture was concentrated and the concentrate was diluted with water and extracted once with ethyl ether. The ether extract (to remove starting material) was discarded. The aqueous solution was acidified with conc HCl and the orange precipitate that resulted was extracted with ethyl ether. The aqueous solution was extracted with ether 3 times. The ether extracts were combined and dried over anhydrous magnesium sulfate, filtered, and concentrated to yield 253.13 g (87.5% yield) of the monoacid.

Step 9

Preparation of methyl 2-(difluoromethyl)-3-chlorocarbonyl-4-(2-methylpropyl)-6-(trifluoromethyl)-5-pyridinecarboxylate. The acid (253 g, 0.7121 mol) from Step 8 was refluxed for 24 hours in approximately 250–300 mL thionyl chloride. The reaction mixture was concentrated to yield 244.59 g of acid chloride in 91.9% yield. $n_D^{25}$ 1.4614.

Steps 1–9 above have illustrated the preparation of pyridine carboxylic acid chlorides having a particular set of 2,6-, and 4-substituents. Preparation of other acid chlorides will be clear from the foregoing and by reference to U.S. Pat. No. 4,692,184.

PREPARATION OF 5-AMINO PYRIDINES

The next step in the sequence for preparing compounds of the present invention is the conversion of the carboxylic acid chloride function of the starting materials shown above to the corresponding 5-amino or 3,5-bis amino pyridine. The general procedure for this conversion is shown in Examples A-1 to A-7.

EXAMPLE A-1

3-Pyridinecarboxylic acid, 5-amino-2-(difluoromethyl)-4-(2-methylpropyl)-6-(trifluoromethyl)-, methyl ester. To a stirred solution of 24.4 g (0.375 mol) sodium azide in 100 mL water and 200 mL acetone at room temperature was added a solution of 55.8 g (0.15 mol) of the product of Step 7 above in 100 mL acetone in portions. Following a mild exotherm, the mixture was stirred at room temperature for 4 h. The reaction mixture was concentrated, and diluted with 200 mL water. The mixture was extracted with ethyl ether (2×200 mL), and the combined extracts were washed with water (2×200 mL), dried over magnesium sulfate, and evaporated. The crude product was then vacuum distilled (130° C., 2 mmHg) by kugelrohr apparatus to afford 44.0 g (91%) of the desired product as a pale yellow solid. m.p. 48°-50° C.

The following amines were made in a similar manner using the general procedure for Example A-1 and starting with the indicated pyridine acid chloride.

EXAMPLE A-2

3-Pyridinecarboxylic acid. 5-amino-4-cyclobutyl-2-(difluoromethyl)-6-(trifluoromethyl)-, methyl ester. A 90% yield from 3-pyridinecarboxylic acid, 5-chlorocarbonyl-4-cyclobutyl-2-(difluoromethyl)-6-(trifluoromethyl)-, methyl ester. m.p. 89°-93° C.

EXAMPLE A-3

3-Pyridinecarboxylic acid, 5-amino-2-(difluoromethyl)-4-methyl-6-(trifluoromethyl)-, methyl ester. A 61% yield from 3-pyridinecarboxylic acid, 5-chlorocarbonyl- 2-(difluoromethyl)-4-methyl-6-(trifluoromethyl)-, methyl ester. $n_D^{25}=1.5844$.

EXAMPLE A-4

3-Pyridinecarbonitrile. 5-amino-6-(difluoromethyl)-4-(2-methylpropyl)-2-(trifluoromethyl)-. An 89% yield from 3-pyridinecarbonitrile, 5-chlorocarbonyl-6-(difluoromethyl)-4-(2-methylpropyl)-2-(trifluoromethyl)-.

EXAMPLE A-5

3-Pyridinecarboxylic acid, 5-amino-2-(difluoromethyl)-4-(cyclopropylmethyl)-6-(trifluoromethyl)-, methyl ester. A 65% from 3-pyridinecarboxylic acid, 5-chlorocarbonyl-4-(cyclopropylmethyl)-2-(difluoromethyl)-6-(trifluoromethyl)-, methyl ester. $n_D^{25}=1.5885$.

EXAMPLE A-6

3-Pyridinecarbothioic acid. 5-amino-2-(difluoromethyl)-4-(2-methylpropyl)-6-(trifluoromethyl)-, S-methyl ester. An 83% yield from 3-pyridinecarbothioic acid, 5-chlorocarbonyl-2-(difluoromethyl)-4-(2-methylpropyl)-6-(trifluoromethyl)-, S-methyl ester. $n_D^{25}=1.5846$.

EXAMPLE A-7

3,5-Pyridinediamine, 2-(difluoromethyl)-4-(2-methylpropyl)-6-(trifluoromethyl). A 97% yield from 3,5-bis-(chlorocarbonyl)-2-(difluoromethyl)-4-(2-methylpropyl)-6-(trifluoromethyl)pyridine, the product of Step 6 above, as a dark oil; used in further steps without purification, since this material is unstable.

PREPARATION OF COMPOUNDS OF THE INVENTION

The haloalkyl carboxamide and haloethoxy carboxamide (or haloethyl carbamate) compounds of this invention are made as shown in the following Examples 1 to 25. Examples 1–20 illustrate the preparation of the haloalkyl carboxamide compounds, while Examples 23–25 illustrate synthesis of the haloethoxy carboxamide, or haloethyl carbamate, compounds.

EXAMPLE 1

3-Pyridinecarboxylic acid, 5-[(4-bromo-1-oxobutyl)amino]-4-cyclobutyl-2-(difluoromethyl)-6-(trifluoromethyl)-, methyl ester. A stirred mixture of 5.10 g (0.016 mol) of product of Example A-2 and 3.63 g (0.020 mol) 4-bromobutyryl chloride in 40 mL anhydrous toluene was refluxed overnight. The mixture was allowed to cool to room temperature. Upon cooling, the precipitated product was collected by vacuum filtration on a Buchner funnel. Recrystallization in ethyl acetate-hexane provided 4.92 g (66%) of the desired product as an off-white solid. m.p. 167°-169° C.

The amide compound in Example 2 and the haloamide compounds of Examples 3 to 20 below were prepared using the same general procedure as that of Example 1.

EXAMPLE 2

3-Pyridinecarboxylic acid, 2-(difluoromethyl)-4-(2-methylpropyl)-5-(4,5-dibromo-1-oxopentyl)amino]-6-(trifluoromethyl)-, methyl ester. The product of Example A-1 was reacted with 4-pentenoic acid chloride in THF solution at 75° C. for 3 days for a 63% yield of 3-pyridinecarboxylic acid, 2-(difluoromethyl)-4-(2-methylpropyl)-5-[(1-oxo-4-pentenyl)amino]-6-(trifluoromethyl)-, methyl ester. m.p. 122°-124° C.

To a mixture of 3.38 g (0.0083 mol) of this compound in 100 mL carbon tetrachloride was added sufficient methylene chloride to dissolve the amide completely. To this solution was added a solution of 1.32 g (0.0083 mol) bromine in 25 mL carbon tetrachloride dropwise at room temperature. Following the addition, the reaction mixture was partitioned with 100 mL 25% sodium thiosulfate solution, and the layers were separated. The organic layer was dried over magnesium sulfate and evaporated to yield the title compound.

EXAMPLE 3

3-Pyridinecarbothioic acid, 5-(4-bromo-1-oxobutyl)amino]-2-(difluoromethyl)-4-(2-methylpropyl)-6-(trifluoromethyl)-, S-methyl ester. A 65% yield from the product of Example A-6 and 4-bromobutyryl chloride with a reaction time of 12 hours. m.p. 147°-148 ° C.

EXAMPLE 4

3-Pyridinecarboxylic acid, 5-[(5-bromo-1-oxopentyl)amino]-2-(difluoromethyl)-4-(2-methylpropyl)-6-(trifluoromethyl)-, methyl ester. A 26% yield from the product of Example A-1 and 5-bromopentanoyl chloride with a reaction time of 48 hours. m.p. 94°-96° C.

EXAMPLE 5

3-Pyridinecarboxylic acid, 5-[(4-chloro-2-methyl-1-oxobutyl)amino]-2-(difluoromethyl)-4-(2-methylpropyl)-6-(trifluoromethyl)-, methyl ester. A 55% yield from the product of Example A-1 and 4-chloro-2-methylbutyryl chloride with a reaction time of 48 hours. m.p. 18°-120° C.

EXAMPLE 6

3-Pyridinecarboxylic acid, 5-[(4-chloro-3-methyl-1-oxobutyl)amino1-2-(difluoromethyl)-4-(2-methylpropyl)-6-(trifluoromethyl), methyl ester. A 29% yield from the product of Example A-1 and 4-chloro-3-methylbutanoyl chloride with a reaction time of 48 hours. m.p. 109°-111° C.

EXAMPLE 7

3-Pyridinecarboxylic acid, 5-[2,4-dichloro-1-oxobutyl)-amino]-2-(difluoromethyl)-4-(2-methylpropyl)-6-(trifluoromethyl)-, methyl ester. A yield of 68% from the product of Example A-1 and 2,4-dichlorobutanoyl chloride with a reaction time of 12 hours. m.p. 104°-106° C.

EXAMPLE 8

3-Pyridinecarboxylic acid, 5-[(4-bromo-2-methylene-1-oxobutyl)amino[-2-(difluoromethyl)-4-(2-methylpropyl)- 6-(trifluoromethyl)-, methyl ester. A yield of 48% from the product of Example A-1 and 4-bromo-2-(bromomethyl)-butanoyl chloride with a reaction time of 4 days. m.p. 106°-108° C.

EXAMPLE 9

3-Pyridinecarboxylic acid, 5-[(4-bromo-2-methyl-1-oxobutyl)amino1-2-(difluoromethyl)-4-(2-methylpropyl)-6-(trifluoromethyl)-, methyl ester. A yield of 81% from the product of Example A-1 and 4-bromo-2-methylbutanoyl chloride with the reaction run neat at 60° C. overnight. m.p. 120°-122° C.

EXAMPLE 10

3-Pyridinecarboxylic acid, 5-[(4-bromo-2-fluoro-1-oxobutyl)amino1-2-(difluoromethyl)-4-(2-methylpropyl)-6-(trifluoromethyl), methyl ester. An 89% yield from the product of Example A-1 and 4-bromo-2-fluorobutanoyl chloride at 60° C. overnight. m.p. 121°-122° C.

EXAMPLE 11

3-Pyridinecarboxylic acid, 5-[(4-bromo-1-oxobutyl)-amino]-2-(difluoromethyl)-4-methyl-6-(trifluoromethyl)-, methyl ester. A yield of 96% from the product of Example A-3 and 4-bromobutanoyl chloride at 60° C. overnight. m p. 98°-100° C.

EXAMPLE 12

Butanamide, N,N'-[2-(difluoromethyl1-4-(2-methylpropyl)-6-(trifluoromethyl)-3,5-pyridinediyl[bis(4-bromo-. A yield of 32% from the product of Example A-7 and 4-bromobutanoyl chloride at room temperature overnight. m.p. 234° C. with decomposition.

EXAMPLE 13

Butanamide, 4-bromo-N-[5-cyano-2-(difluoromethyl)-4-(2-methylpropyl)-6-(trifluoromethyl)-3-pyridinyl]-. A yield of 64% from the product of Example A-4 and 4-bromobutanoyl chloride. m.p. 175°-180° C.

EXAMPLE 14

3-Pyridinecarboxylic acid, 5-[[4-bromo-2-(methylthio)-1-oxobutyl]amino]-2-(difluoromethyl)-4-(2-methylpropyl)-6-(trifluoromethyl)-, methyl ester. A yield of 61% from the product of Example A-1 and 4-bromo-2-(methylthio)-butanoyl chloride at 60°-80° C. for 30 hours. m.p. 103°-105° C.

EXAMPLE 15

3-Pyridinecarbothioic acid, 5-[(4-bromo-2-methyl-1-oxobutyl)amino1-2-(difluoromethyl)-4-(2-methylpropyl)-6-(trifluoromethyl -. S-methyl ester. A 97% yield from the product of Example A-6 and 4-bromo-2-methyl butanoyl chloride. m.p. 120°-121° C.

EXAMPLE 16

3-Pyridinecarboxylic acid, 5-[(4-bromo-2,2-dimethyl-1-oxobutyl)amino1-2-(difluoromethyl)-4-(2-methylpropyl)-6-(trifluoromethyl)-, methyl ester. A yield of 33% from the product of Example A-1 and 4-bromo-2,2-dimethyl-butanoyl chloride with a reaction time of 96 hours.

EXAMPLE 17

3-Pyridinecarboxylic acid, 5-[(2-bromo-4-iodo-1-oxobutyl)amino1-2-(difluoromethyl)-4-(2-methylpropyl)-6-(trifluoromethyl)-, methyl ester. A stirred mixture of 5.62 g (0.010 mol) of the product of Example 20 and 1.63 g (0.011 mol) of sodium iodide in 30 mL acetone was refluxed for 1 hour. The solvent was evaporated, and the residue was partitioned between water (100 mL) and ethyl ether (150 mL). The organic layer was washed with water (2×30 mL), dried over magnesium sulfate and evaporated. The crude material was filtered through silica gel, and trituration of the oily residue with hexane/ethyl ether afforded 4.72 g (78%) of the desired product as a white solid. m.p. 111°-113° C.

EXAMPLE 18

3-Pyridinecarboxylic acid, 5-[4-bromo-1-(oxobutyl) amino]-2-(difluoromethyl)-4-(2-methylpropyl)-6-(trifluoromethyl)-, methyl ester. A yield of 72% from the product of Example A-1. m.p. 95°-96° C.

EXAMPLE 19

3-Pyridinecarboxylic acid, 5-[(4-bromo-1-oxobutyl) amino]-4-(cyclopropylmethyl)-2-(difluoromethyl)-6-(trifluoromethyl)-, methyl ester. A 70% yield from the product of Example A-5. m.p. 60°-61° C.

EXAMPLE 20

3-Pyridinecarboxylic acid. 5-(2,4-dibromo-1-oxobutyl)amino]-2-(difluoromethyl)-4-(2-methylpropyl)-6-(trifluoromethyl)-, methyl ester. A yield of 31% from the product of Example A-1 and 2,4-dibromobutyryl chloride with a reaction time of 72 hours. m.p. 113°-115° C.

EXAMPLE 21

3-Pyridinecarboxylic acid. 5-[(4-chloro-1-oxobutylamino1-2-(difluoromethyl)-4-(2-methylpropyl)6-(trifluoromethyl)-, methyl ester. A yield of 70% from the product of Example A-1 and 4-chlorobutyryl chloride with a reaction time of 72 hours. m.p. 90°-92° C.

EXAMPLE 22

3-Pyridinecarboxylic acid, 2-(difluoromethyl)-5-[(4-iodo-1-oxobutyl)amino]-4-(2-methylpropyl)-6-(trifluoromethyl)-, methyl ester. To a stirred solution of 2.5 g (0.005 mol) of the product of Example 18 in 30 mL acetone was added 1.25 g (0.008 mol) sodium iodide, and the mixture was refluxed for 3 hrs. Following this period, the solvent was evaporated, and the residue was partitioned between 100 mL ether and 50 mL water. The ether layer was washed with water, dried over anhydrous magnesium sulfate, and evaporated. Trituration of the residue with hexane-ether afforded 2.03 g of the desired product, a 74% yield, as a white crystalline solid. m.p. 109°-110° C.

The following Examples 23-25 show the haloethyl carbamate compounds of this invention which are precursor compounds to the cyclic imidate compounds containing two oxygen atoms in the heterocycle attached to the pyridine ring. Each of these compounds is prepared by reaction of a chlorocarbonyl pyridine with sodium azide in the presence of an appropriate 1,2-diol to form a hydroxyethyl carbamate (Step A), followed by chlorination (Step B). Example 23 shows the procedure in detail, and the compounds of Examples 24 and 25 are prepared similarly.

EXAMPLE 23

3-Pyridinecarboxylic acid, 5-[[2-chloroethoxy)carbonyl]amino]-2-(difluoromethyl)-4-(2-methylpropyl)-6-(trifluoromethyl)-, methyl ester.

Step A

To a stirred suspension of 7.8 g (0.12 mol) sodium azide in a mixture of 100 mL ethylene glycol and 100 mL acetone was added a solution of 18.6 g (0.05 mol) of the 5-chlorocarbonyl pyridine shown in Step 7 above in 50 mL acetone in small portions. The reaction mixture was stirred at room temperature overnight, and then concentrated to remove most of the acetone. The mixture was diluted with water and extracted with three 200 mL portions of ethyl acetate. The combined organic layers were washed with water, dried over anhydrous magnesium sulfate, and evaporated. Purification of the residue by HPLC gave 16.6 g (80%) of the desired intermediate, 3-pyridinecarboxylic acid, 2-(difluoromethyl)-5-[[(2-hydroxyethoxy)carbonyl]amino]-4-(2-methylpropyl)-6-(trifluoromethyl)-, methyl ester, as a white solid. m.p. 104° C.

Step B

A solution of 13.6 g (0.033 mol) of product of Step A in 100 mL thionyl chloride was refluxed for 4 h. The solution was then evaporated and the residue was partitioned between 200 mL chloroform and 200 mL water. The organic layer was dried over anhydrous magnesium sulfate and evaporated. Purification of the residue by HPLC afforded 10.6 g (74%) of title compound as a white solid. m.p. 95°-96° C.

EXAMPLE 24

3-Pyridinecarboxylic acid, 5-[[(2-chloropropoxy)-carbonyl]amino]-2-(difluoromethyl)-4-(2-methylpropyl)-6-(trifluoromethyl)-, methyl ester.

Step A

3-Pyridinecarboxylic acid, 2-(difluoromethyl)-5-[[(2-hydroxypropoxy)carbonyl]amino]-4-(2-methylpropyl)-6-(trifluoromethyl)-, methyl ester, was obtained in a 63% yield from the product of Step 7 above and sodium azide in propylene glycol/acetone. m.p. 97°-99° C.

Step B

The title product was obtained in a 79.8% yield from the product of Step A. m.p. 94°-96° C.

EXAMPLE 25

3-Pyridinecarboxylic acid, 5-(3-chloro-2-butoxy)-carbonylamino]-2-(difluoromethyl)-4-(2-methylpropyl)-6-(trifluoromethyl)-, methyl ester.

Step A

3-Pyridinecarboxylic acid, 2-(difluoromethyl)-5-[[2-hydroxy-1-methylpropoxy)carbonyl]amino]-4-(2-methyl propyl)-6-(trifluoromethyl), methyl ester, was obtained in a 52.5% yield from the product of Step 7 above and sodium azide in 2,3-butanediol/acetone. m.p. 137°-138° C.

Step B

The title compound was obtained in an 88% yield from the product of Step A. m.p. 108°-110° C.

PREPARATION OF CYCLIC IMIDATE COMPOUNDS

Preparation of the pyridine cyclic imidate compounds from the haloalkyl carboxamide and haloethoxy carboxamide compounds of this invention is shown in the following Examples P-1 to P-22.

EXAMPLE P-1

3-Pyridinecarboxylic acid, 2-(difluoromethyl)-4-(2-methylpropyl)-5-tetrahydro-2H-ran-2-ylidene)amino]-6-(trifluoromethyl)-, methyl ester. To a stirred solution of 2.87 g (0.0059 mol) of the product of Example 4 in 75 mL methylene chloride was added 1.30 g (0.0067 mol) silver tetrafluoroborate in one portion at room temperature. The resulting slurry was stirred for 30 min., followed by addition of 100 mL of sat. sodium bicarbonate solution for an additional 30 min. The mixture was vacuum filtered through a celite pad to remove the precipitated silver salts. The filtrate layers were separated, and the organic layer was dried over magnesium sulfate and evaporated. The crude material was purified by HPLC (20% ethyl acetate-hexane) to afford 1.60 g (67%) of the desired product as a pale yellow wax. $n_D^{25} = 1.58475$.

EXAMPLE P-2

3-Pyridinecarboxylic acid, 2-(difluoromethyl)-5-(dihydro-3-methyl-2(3H)-furanylidene)amino]-4-(2-methylpropyl)-6-(trifluoromethyl)-, methyl ester. To a stirred solution of 2.00 g (0.0045 mol) of the product of Example 5 in 25 mL methylene chloride was added 1.05 g (0.0054 mol) silver tetrafluoroborate in one portion. The resulting slurry was stirred for 1 h, and this was followed by the addition of 100 mL sat. sodium bicarbonate and stirring for an additional 30 min. The mixture was filtered through celite to remove the precipitated silver salts, and the layers were separated. The organic layer was dried over magnesium sulfate and evaporated. The residue was purified by chromatography (20% ethyl acetate-hexane) to afford 1.30 g (71%) of the desired product as a clear colorless wax. $n_D^{25} = 1.5820$.

This compound may be similarly prepared using the product of Example 9.

The following compounds of Examples P-3 to P-16 were made by the same general procedures as those shown above in Examples P-1 and P-2.

EXAMPLE P-3

3-Pyridinecarboxylic acid, 2-(difluoromethyl)-5-[dihydro-4-methyl-2(3H1-furanylidene)amino]-4-(2-methylpropyl)-6-(trifluoromethyl)-, methyl ester. An 84% yield from the product of Example 6. $n_D^{25} = 1.5822$.

EXAMPLE P-4

3-Pyridinecarboxylic acid, 5-[(3-bromodihydro-2(3H)-furanylidene)amino1-2-(difluoromethyl)-4-(2-methylpropyl)-6-(trifluoromethyl)-, methyl ester. A 64% yield from the product of Example 17. $n_D^{25} = 1.5842$.

EXAMPLE P-5

3-Pyridinecarboxylic acid, 5-[3-chlorodihydro-2-(3H)-furanylidene)amino]-2-(difluoromethyl)-4-(2-methylpropyl)-6-(trifluoromethyl)-, methyl ester. A yield of 77% from the product of Example 7. $n_D^{25}$ 1.5836.

EXAMPLE P-6

3-Pyridinecarboxylic acid, 2-(difluoromethyl)-5-[(dihydro-3,3-dimethyl-2(3H)-furanylidene)amino]-4-(2-methylpropyl)-6-(trifluoromethyl)-, methyl ester. A yield of 34% from the product of Example 16. $n_D^{25}$ 1.5850.

EXAMPLE P-7

3-Pyridinecarboxylic acid. 2-(difluoromethyl)-5-[3-fluorodihydro-2(3H)-furanylidene)amino]-4-(2-methylpropyl)-6-(trifluoromethyl)-. methyl ester. A yield of 80% from the product of Example 10. $n_D^{25}$ 1.5825.

EXAMPLE P-8

3-Pyridinecarboxylic acid. 2-(difluoromethyl)-5-(dihydro-3-methylene-2(3H)-furanylidene)amino]-4-(2-methylpropyl)-6-(trifluoromethyl)-, methyl ester. A yield of 66% from the product of Example 8. $n_D^{25}$ 1.5802.

EXAMPLE P-9

3-Pyridinecarboxylic acid, 2-(difluoromethyl)-5-[(dihydro-2(3H)-furanylidene)amino]-4-methyl-6-(trifluoromethyl)-, methyl ester. A yield of 79% from the product of Example 11. $n_D^{25}$ 1.5842.

EXAMPLE P-10

3,5-Pyridinediamine, 2-(difluoromethyl)-N,N'-bis(dihydro-2(3H)-furanylidene)-4-(2-methylpropyl)-6-(trifluoromethyl)-. A yield of 84% from the product of Example 12. m.p. 98°–102° C.

EXAMPLE P-11

3-Pyridinecarbonitrile, 6-(difluoromethyl)-5-[(dihydro-2(3H)-furanylidene)amino]-4-(2-methylpropyl)-6-(trifluoromethyl)-. A yield of 55% from the product of Example 13. m.p. 68°–69° C.

EXAMPLE P-12

3-Pyridinecarboxylic acid, 2-(difluoromethyl)-5-[(dihydro-3-(methylthio)-2-(3H)-furanylidene)amino]-4-(2-methylpropyl)-6-(trifluoromethyl), methyl ester. A yield of 81% from the product of Example 14. $n_D^{25}$ 1.5860.

EXAMPLE P-13

3-Pyridinecarboxylic acid, 4-cyclobutyl-2-(difluoromethyl)-5-[(dihydro-2(3H)-furanylidene)amino]-6-(trifluoromethyl)-, methyl ester. A yield of 56% from the product of Example 1. $n_D^{25}$ 1.5861.

EXAMPLE P-14

3-Pyridinecarbothioic acid. 2-(difluoromethyl)-5-[(dihydro-2(3H)-furanylidene)amino]-4-(2-methylpropyl)- 6-(trifluoromethyl)-, S-methyl ester. A yield of 72% from the product of Example 3. m.p. 89°–91° C.

EXAMPLE P-15

3-Pyridinecarboxylic acid. 2-(difluoromethyl)-5-(dihydro-2(3H)-furanylidene)amino]-4-(2-methylpropyl)-6-(trifluoromethyl)-, methyl ester. A yield of 71% from the product of Example 18. $n_D^{25}$ 1.5876.

EXAMPLE P-16

3-Pyridinecarboxylic acid. 4-(cyclopropylmethyl)-2-(difluoromethyl)-5-[(dihydro-2(3H)-furanylidene)amino]-6-(trifluoromethyl)-. methyl ester. A yield of 91% from the product of Example 19. $n_D^{25}$ 1.5865.

EXAMPLE P-17

3-Pyridinecarboxylic acid, 5-[[5-(bromomethyl)dihydro-2(3H)-furanylidene]amino]-2-(difluoromethyl)-4-(2-methylpropyl)-6-(trifluoromethyl)-, methyl ester.

The crude product of Example 2 was dissolved in 50 mL methylene chloride. To this solution was added 1.62 g (0.0083 mol) silver tetrafluoroborate with stirring in one portion. After 30 min, saturated sodium bicarbonate solution (50 mL) was added with stirring for an additional 10 min. The reaction mixture was vacuum filtered through celite and the layers were separated. The organic layer was dried over magnesium sulfate and evaporated. The crude material was purified by HPLC (20% ethyl acetate/hexane) to afford 3.19 g (79%) of the desired product as a pale yellow viscous oil. $n_D^{25}$ 1.5827.

EXAMPLE P-18

3-Pyridinecarbothioic acid, 2-(difluoromethyl)-5-(dihydro-2(3H)-thienylidene)amino]-4-(2-methylpropyl)-6-(trifluoromethyl)-, S-methyl ester. A slurry of 5.51 g (0.011) of the product of Example 3 and 2.45 g (0.012 mol) phosphorus pentachloride in 60 mL carbon tetrachloride was stirred overnight at room temperature. The resulting clear solution was concentrated in vacuo to afford 5.70 g (100%) of the desired intermediate as a clear oil with no further purification necessary. A slurry of this oil and 0.72 g (0.016 mol) of lithium sulfide in 30 mL anhydrous THF was stirred at room temperature overnight. The solvent was evaporated, and the residue was partitioned with ethyl ether (150 mL) and 10% HCl (150 mL). The organic layer was dried over magnesium sulfate and evaporated. The crude material was purified by HPLC (15% ethyl acetate/hexane) to afford 1.54 g (35%) of the desired product as a clear wax. $n_D^{25}$ 1.5842.

EXAMPLE P-19

3-Pyridinecarbothioic acid, 2-(difluoromethyl)-5-[(dihydro-3-methyl-2(3H)-furanylidene)amino]-4-(2-methylpropyl)-6-(trifluoromethyl)-S-methyl ester. A yield 42% from the product of Example 15. $n_D^{25}$ 1.5950.

EXAMPLE P-20

3-Pyridinecarboxylic acid, 2-(difluoromethyl)-5-(1,3-dioxolan-2-ylidene)amino-4-(2-methylpropyl)-6-(trifluoromethyl)-, methyl ester. To a solution of 6.48 g (0.015 mol) of the product of Example 23 in 200 mL methylene chloride was added 3.3 g (0.017 mol) silver tetrafluoroborate in one portion. The resulting suspension was stirred at room temperature for 10 h after which 200 mL saturated sodium bicarbonate solution was added and stirring was continued for an additional 45 min. The mixture was filtered to remove insoluble salts and the salts were washed with 200 mL methylene chloride. The organic layer in the combined filtrates was separated, dried over anhydrous magnesium sulfate, and evaporated. Purification of the residue by HPLC afforded 5.5 g (92.6%) of title compound as a white solid. m.p. 101°–102° C.

Examples P-21 and P-22 were each prepared similarly to Example P-20.

EXAMPLE P-21

3-Pyridinecarboxylic acid, 2-(difluoromethyl)-5-[(4-methyl-1,3-dioxolan-2-ylidene)amino]-4-(2-methylpropyl)-6-(trifluoromethyl)-, methyl ester. A 73% yield from the product of Example 24 as a colorless oil. $n_D^{25}$ 1.5955.

EXAMPLE P-22

3-Pyridinecarboxylic acid, 2-(difluoromethyl)-5-[(4,5-dimethyl-1,3-dioxolan-2-ylidene)amino]-4-(2-methylpropyl)-6-(trifluoromethyl)-, methyl ester. A 75.5% yield from the product of Example 25 as a colorless oil. $n_D^{25}$ 1.5982.

PRE-EMERGENCE HERBICIDE EXAMPLES

As noted above, many of the compounds of this invention have been found to be effective as herbicides, particularly pre-emergence herbicides.

The tests for pre-emergence herbicide activity are conducted as follows:

Topsoil is placed in an aluminum pan and compacted to a depth of 0.95 to 1.27 cm. from the top of the pan. On the top of the soil is placed a predetermined number of seeds of each of several monocotyledonous and dicotyledonous annual plant species and/or vegetative propagules of various perennial plant species. The soil required to level fill a pan after seeding or adding vegetative propagules is weighed into another pan. A known amount of the active ingredient dissolved or suspended in an organic solvent or water and applied in acetone or water as a carrier is thoroughly mixed with this cover soil, and the herbicide/soil mixture is used as a cover layer for the previously prepared pan. In Table 1 below the for example, amount of active ingredient applied in the cover layer soil is equal to an application rate of 11.2 kg/ha. After treatment, the pans are moved to a greenhouse bench where they are watered from below as needed to give adequate moisture for germination and growth.

Approximately 10–14 days (usually 11 days) after seeding and treating, the pans are observed and the results (% inhibition) are recorded.

Table 1 below summarizes the results of the pre-emergence herbicidal activity tests of compounds of this invention in weeds. The herbicidal rating shown in Table 1 is a measure of the percent inhibition of each plant species according to the following rating scale:

| Plant Response | Index |
| --- | --- |
| 0–24% inhibition | 0 |
| 25–49% inhibition | 1 |
| 50–74% inhibition | 2 |
| 75–100% inhibition | 3 |
| Species not planted | — |
| Species planted, no data | N |

The plant species usually regarded as weeds which are utilized in one set of tests, the data for which are shown in Table 1, are identified by letter headings above the columns in accordance with the following legend:

Yens - Yellow nutsedge
Anbg - Annual bluegrass
Sejg - Seedling johnsongrass
Dobr - Downy Brome
Bygr - Barnyardgrass
Mogl - Morningglory
Cobu - Cocklebur
Vele - Velvetleaf
Inmu - Indian mustard
Wibw - Wild buckwheat
Cath - Canada thistle
Colq - Common lambsquarters
Pesw - Pennsylvania smartweed
Rhqg - Rhizome quackgrass
Rhjg - Rhizome johnsongrass

TABLE 1

PRE-EMERGENCE HERBICIDE DATA

| Ex. No. | Rate kg/ha | Yens | Abng | Sejg | Dobr | Bygr | Mogl | Cobue | Vlee | Inmuw | Wbuw | Cath | Colgw | Pehsqw | Rhqg | Rhjg |
|---|---|---|---|---|---|---|---|---|---|---|---|---|---|---|---|---|
| 1  | 11.21 | 2 | 3 | 3 | 3 | 3 | 3 | 1 | 3 | 3 | 3 | | | | | |
| 3  | 11.21 | 1 | 3 | 3 | 3 | 3 | 3 | 0 | 3 | 3 | 3 | | | | | |
| 4  | 11.21 | 1 | 3 | 3 | 3 | 3 | 1 | 0 | 2 | 3 | 3 | | | | | |
| 5  | 11.21 | 3 | 3 | 3 | 3 | 3 | 3 | 2 | 3 | 3 | 3 | | | | | |
| 6  | 11.12 | 2 | 3 | 3 | 3 | 3 | 3 | 0 | 2 | 3 | 3 | | | | | |
| 7  | 11.21 | 3 | 3 | 3 | 3 | 3 | 3 | 0 | 3 | 3 | 3 | | | | | |
| 8  | 11.21 | 2 | 3 | 3 | 3 | 3 | 2 | 1 | 3 | 3 | 3 | | | | | |
| 10 | 11.21 | 2 | 3 | 3 | 3 | 3 | 3 | 2 | 3 | 3 | 3 | | | | | |
| 11 | 11.21 | 0 | 0 | 3 | 0 | 2 | 3 | 0 | 1 | 1 | 0 | | | | | |
| 12 | 11.21 | 0 | 3 | 3 | 0 | 3 | 0 | 0 | 0 | 0 | 0 | | | | | |
| 13 | 11.21 | 0 | 0 | 2 | 0 | 3 | 2 | 0 | 0 | 1 | 0 | | | | | |
| 14 | 11.21 | 0 | 3 | 3 | 3 | 3 | 1 | 0 | 1 | 3 | 3 | | | | | |
| 15 | 11.21 | 2 | 3 | 3 | 2 | 3 | 3 | 2 | 3 | 3 | 3 | | | | | |
| 17 | 11.21 | 0 | 3 | 3 | 3 | 3 | 3 | 2 | 3 | 3 | 2 | | | | | |
| 18 | 11.21 | 2 | | | 3 | 3 | 3 | 3 | 3 | | | 3 | 3 | 3 | 3 | 0 |
| 19 | 11.21 | 3 | | | 3 | 3 | 3 | 3 | 3 | | | 3 | 3 | N | 3 | 2 |
| 20 | 11.21 | 0 | 3 | 3 | 2 | 3 | 3 | 0 | 3 | 3 | 3 | | | | | |
| 21 | 11.21 | 0 | 3 | 3 | 2 | 3 | 2 | 1 | 2 | 2 | 2 | | | | | |
| 22 | 11.21 | 2 | 3 | 3 | 3 | 3 | 3 | 2 | 3 | 3 | 3 | | | | | |
| 23 | 11.21 | 0 | 3 | 3 | 2 | 3 | 3 | 0 | 2 | 0 | 2 | | | | | |
| 24 | 11.21 | 3 | 3 | 3 | 3 | 3 | 2 | 0 | 3 | 2 | 2 | | | | | |

POST-EMERGENCE HERBICIDE EXAMPLES

The post-emergence herbicidal activity of some of the various compounds of this invention was demonstrated by greenhouse testing in the following manner. Topsoil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a bench in the greenhouse and watered from below as needed. After the plants reach the desired age (two to three weeks), each pan, is removed individually to a spraying chamber and sprayed by means of an atomizer, operating at a spray pressure of 170.3 kPa (10 psig) at the application rates noted. In the spray solution is an amount of an emulsifying agent mixture to give a spray solution or suspension which contains about 0.4% by volume of the emulsifier. The spray solution or suspension contains a sufficient amount of the candidate chemical in order to give application rates of he active ingredient corresponding to those shown in the Tables while applying a total amount of solution or suspension equivalent to 1870 L/Ha (200 gallons/acre). The pans were returned to the greenhouse and watered as before and the injury to the plants as compared to the control is observed at approximately 10-14 days (usually 11 days) and in some instances observed again at 24-28 days (usually 25 days) after spraying. The post-emergent herbicidal activity index used in Table 2 is a follows:

| Plant Response | Index |
|---|---|
| 0–24% inhibition | 0 |
| 25–49% inhibition | 1 |
| 50–74% inhibition | 2 |
| 75–99% inhibition | 3 |
| 100% inhibition | 4 |
| Species not planted | — |
| Species planted, no data | N |

TABLE 2

PRE-EMERGENCE HERBICIDE DATA

| Ex. No. | Rate kg/ha | Yens | Abng | Sejg | Dobr | Bygr | Mogl | Cobue | Vlee | Inmuw | Wbuw | Cath | Colgw | Pehsqw | Rhqg | Rhjg |
|---|---|---|---|---|---|---|---|---|---|---|---|---|---|---|---|---|
| 1  | 11.21 | 0 | 0 | 0 | 0 | 1 | 0 | 1 | 0 | 0 | 0 | | | | | |
| 3  | 11.21 | 0 | 0 | 2 | 1 | 1 | 1 | 1 | 2 | 2 | 2 | | | | | |
| 4  | 11.21 | 0 | 0 | 0 | 0 | 0 | 1 | 0 | 0 | 0 | 0 | | | | | |
| 5  | 11.21 | 0 | 1 | 0 | 0 | 0 | 0 | 0 | 0 | 2 | 2 | | | | | |
| 6  | 11.12 | 0 | 0 | 0 | 0 | 0 | 0 | 0 | 0 | 0 | 0 | | | | | |
| 7  | 11.21 | 0 | 0 | 0 | 0 | 0 | 0 | 1 | 1 | 0 | 1 | | | | | |
| 8  | 11.21 | 0 | 0 | 0 | 0 | 0 | 0 | 0 | 0 | 0 | 0 | | | | | |
| 10 | 11.21 | 0 | 0 | 0 | 0 | 0 | 0 | 0 | 0 | 0 | 0 | | | | | |
| 11 | 11.21 | 0 | 0 | 0 | 0 | 0 | 0 | 0 | 0 | 0 | 0 | | | | | |
| 12 | 11.21 | 0 | 0 | 0 | 0 | 0 | 0 | 0 | 0 | 0 | 0 | | | | | |
| 10 | 11.21 | 0 | 0 | 0 | 0 | 0 | 0 | 0 | 0 | 0 | 0 | | | | | |
| 14 | 11.21 | 0 | 0 | 1 | 0 | 0 | 2 | 0 | 1 | 0 | 0 | | | | | |
| 15 | 11.21 | 0 | 0 | 2 | 0 | 0 | 2 | 2 | 0 | 2 | 1 | | | | | |
| 17 | 11.21 | 0 | 0 | 0 | 0 | 0 | 1 | 1 | 1 | 0 | 0 | | | | | |
| 18 | 11.21 | 0 | | | 0 | 0 | 0 | 1 | 0 | | | 0 | 2 | 0 | 0 | 0 |
| 19 | 11.21 | 0 | | | 0 | 0 | 1 | 0 | 1 | | | 0 | 0 | N | 0 | 0 |
| 20 | 11.21 | 0 | 0 | 0 | 0 | 2 | 1 | 2 | 2 | 2 | 2 | | | | | |
| 21 | 11.21 | 0 | 0 | 0 | 0 | 0 | 0 | 0 | 0 | 0 | 0 | | | | | |

TABLE 2-continued

PRE-EMERGENCE HERBICIDE DATA

| Ex. No. | Rate kg/ha | Yens | Anbg | Sejg | Doybr | Bygr | Mogl | Cobu | Vele | Inmb | Wibt | Cath | Colg | Peslw | Rhqg | Rhjg |
|---|---|---|---|---|---|---|---|---|---|---|---|---|---|---|---|---|
| 22 | 11.21 | 0 | 0 | 3 | 0 | 2 | 2 | 2 | 2 | 2 | 2 | | | | | |
| 23 | 11.21 | 0 | 0 | 0 | 0 | 0 | 0 | 0 | 0 | 0 | 0 | | | | | |
| 24 | 11.21 | 0 | 0 | 1 | 0 | 1 | 0 | 0 | 1 | 0 | 0 | | | | | |

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, and polymethylene bisnaphthalene sulfonate. Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring a nonaqueous solution of a water-insoluble active ingredient and an emulsification agent with water until uniform and then homogenizing to give stable emulsion of very finely divided particles. The resulting concentrated aqueous suspension is characterized by its extremely small particle size, so that when diluted and sprayed, coverage is very uniform. Suitable concentrations of these formulations contain from about 0.1-60% preferably 5-50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include dimethylformamide, dimethylsulfoxide, N-methylpyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate extender, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like such as:

Hetetocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine 3-Isopropyl-1H-2,1,3-benzothiadiazin-4-(3H)-one 2,2-dioxide
3-Amino-1,2,4-triazole
6,7-Dihydrodipyrido(1,2-:2',1'-c)-pyrazidinium salt
5-Bromo-3-isopropyl-6-methyluracil
1,1'-Dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate

Ureas

N-(4-chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-1,3,5-triazin-2-yl) aminocarbonyl]-benzenesulfonamide
Methyl 2-(((((4,6-dimethyl-2-pyrimidinyl)amino)-carbonyl)amino)sulfonyl) benzoate
Ethyl 2-[methyl 2-(((((4,6-dimethyl-2-pyrimidinyl)-amino)carbonyl)amino)sulfonyl)]benzoate
Methyl-2((4,6-dimethoxy pyrimidin-2-yl)amino-carbonyl)amino sulfonyl methyl) benzoate
Methyl 2-(((((4-methoxy-6-methyl-1,3,5-triazin-2-yl)amino)carbonyl)amino)sulfonyl) benzoate

Carbamates/Thiolcarbamates

2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl-N,N-diisopropylthiolcarbamate

Acetamides/Acetanilides/Anilines/Amides

2-Chloro-N,N-diallylacetamide
N,N-dimethyl-2,2-diphenylacetamide
N-(2,4-dimethyl-5-[[[(trifluoromethyl)sulfonyl]amino]-phenyl]acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid 2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its salts.
Butyl (R)-2-[4-[(5-(trifluoromethyl)-2-pyridinyl)oxy]-phenoxy]-propanoate

Ethers 2,4-Dichlorophenyl-4-nitrophenyl ether
2-Chloro-δ,δ,δ-trifluoro-p-tolyl-3-ethoxy-4-nitrodiphenyl ether
5-(2-chloro-4-trifluoromethylphenoxy)-N-methyl-sulfonyl 2-nitrobenzamide
1'-(Carboethoxy) ethyl 5-[2-chloro-4-(trifluoromethyl)-phenoxy]-2-nitrobenzoate

Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methyl ethyl)-2-(2-methylphenylmethoxy)-,exo-.

Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | Weight Percent |
|---|---|
| I. Emulsifiable Concentrates | |
| A. Compound of Example No. 3 | 11.0 |
| Free acid of complex organic phosphate or aromatic or aliphatic hydrophobic base (e.g., GAFAC RE-610, registered trademark of GAF Corp.) | 5.59 |
| Polyoxyethylene/polyoxypropylene block copolymer with butanol (e.g., Tergitol XH, registered trademark of Union Carbide Corp.) | 1.11 |
| Phenol | 5.34 |
| Monochlorobenzene | 76.96 |
| | 100.00 |
| B. Compound of Example No. 14 | 25.00 |
| Free acid of complex organic phosphate of aromatic or aliphatic hydrophobic base (e.g., GAFAC RE-610) | 5.00 |
| Polyoxyethylene/polyoxypropylene block copolymer with butanol (e.g., Tergitol XH) | 1.60 |
| Phenol | 4.75 |
| Monochlorobenzene | 63.65 |
| | 100.00 |
| II. Flowables | |
| A. Compound of Example No. 11 | 25.0 |
| Methyl cellulose | 0.3 |
| Silica Aerogel | 1.5 |
| Sodium lignosulfonate | 3.5 |
| Sodium N-methyl-N-oleyl taurate | 2.0 |
| Water | 67.7 |
| | 100.0 |
| B. Compound of Example No. 18 | 45.0 |
| Methyl cellulose | .3 |
| Silica aerogel | 1.5 |
| Sodium lignosulfonate | 3.5 |
| Sodium N-methyl-N-oleyl taurate | 2.0 |
| Water | 47.7 |
| | 100.0 |
| III. Wettable Powders | |
| A. Compound of Example No. 5 | 25.0 |
| Sodium lignosulfonate | 3.0 |
| Sodium N-methyl-N-oleyl-taurate | 1.0 |
| Amorphous silica (synthetic) | 71.0 |

|  | Weight Percent |
| --- | --- |
|  | 100.0 |
| B. Compound of Example 13 | 80.00 |
| Sodium dioctyl sulfosuccinate | 1.25 |
| Calcium lignosulfonate | 2.75 |
| Amorphous silica (synthetic) | 16.00 |
|  | 100.00 |
| C. Compound of Example No. 6 | 10.0 |
| Sodium lignosulfonate | 3.0 |
| Sodium N-methyl-N-oleyl-taurate | 1.0 |
| Kaolinite clay | 86.0 |
|  | 100.0 |
| IV. Dusts | |
| A. Compound of Example No. 14 | 2.0 |
| Attapulgite | 98.0 |
|  | 100.0 |
| B. Compound of Example No. 10 | 60.0 |
| Montmorillonite | 40.0 |
|  | 100.0 |
| C. Compound of Example No. 9 | 30.0 |
| Ethylene glycol | 1.0 |
| Bentonite | 69.0 |
|  | 100.0 |
| D. Compound of Example No. 3 | 1.0 |
| Diatomaceous earth | 99.0 |
|  | 100.0 |
| V. Granules | |
| A. Compound of Example No. 2 | 15.0 |
| Granular attapulgite (20/40 mesh) | 85.0 |
|  | 100.0 |
| B. Compound of Example No. 10 | 30.0 |
| Diatomaceous earth (20/40) | 70.0 |
|  | 100.0 |
| C. Compound of Example No. 12 | 1.0 |
| Ethylene glycol | 5.0 |
| Methylene blue | 0.1 |
| Pyrophyllite | 93.9 |
|  | 100.0 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

Although the invention is described with respect to specific modifications, the details thereof are not to be construed as limitations.

We claim:

1. A compound represented by the formula

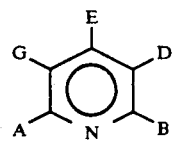

wherein:
one of A and B is selected from the group consisting of fluorinated methyl and chlorofluorinated methyl radicals, and the other is selected from the group consisting of fluorinated methyl, chlorofluorinated methyl and lower alkyl radicals;

E is selected from the group consisting of alkyl, alkenyl, cycloalkyl, cycloalkylalkyl, haloalkyl, and alkylthioalkyl radicals;

G is selected from the group consisting of hydroxycarbonyl, alkoxycarbonyl, haloalkoxycarbonyl, alkylthiocarbonyl, alkenyloxycarbonyl, alkynyloxycarbonyl, cyano, pyridylthiocarbonyl, aminocarbonyl, monoalkylsubstituted aminocarbonyl, and dialkylsubstituted aminocarbonyl, or is the same as D; and D is —NHR in which R is selected from the group consisting of 3-halopropylcarbonyl, 4-halobutylcarbonyl, and 2-haloethoxycarbonyl groups, optionally substituted with one or more groups selected from alkyl, fluoro, chloro, bromo, iodo, alkylidene, alkoxy, alkylthio, and haloalkyl radicals.

2. A compound according to claim 1 wherein one of A and B is trifluoromethyl and the other is difluoromethyl.

3. A compound according to claim 2 wherein E is selected from the group consisting of 2-methylpropyl, cyclobutyl, and cyclopropylmethyl.

4. A compound according to claim 3 wherein R is 3-halopropylcarbonyl, optionally substituted with methyl.

5. A herbicidal composition containing a diluent and a compound represented by the formula

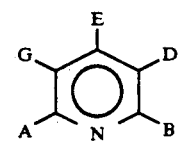

wherein:
one of A and B is selected from the group consisting of fluorinated methyl and chlorofluorinated methyl radicals, and the other is selected from the group consisting of fluorinated methyl, chlorofluorinated methyl and lower alkyl radicals;

E is selected from the group Consisting of alkyl, alkenyl, cycloalkyl, cycloalkylalkyl, haloalkyl, and alkylthioalkyl radicals;

G is selected from the group consisting of hydroxycarbonyl, alkoxycarbonyl, haloalkoxycarbonyl, alkylthiocarbonyl, alkenyloxycarbonyl, alkynyloxycarbonyl, cyano, pyridylthiocarbonyl, aminocarbonyl, monoalkylsubstituted aminocarbonyl, and dialkylsubstituted aminocarbonyl, or is the same as D; and D is —NHR in which R is selected from the group consisting of 3-halopropylcarbonyl, 4-halobutylcarbonyl, and 2-haloethoxycarbonyl groups, optionally substituted with one or more groups selected from alkyl, fluoro, chloro, bromo, iodo, alkylidene, alkoxy, alkylthio, and haloalkyl radicals.

6. A composition according to claim 5 wherein one of A and B is trifluoromethyl and the other is difluoromethyl.

7. A composition according to claim 6 wherein E is selected from the group consisting of 2-methylpropyl, cyclobutyl, and cyclopropylmethyl.

8. A composition according to claim 7 wherein R is 3-halopropylcarbonyl, optionally substituted with methyl.

9. A method of controlling undesirable vegetation which comprises applying to the plant locus an effective amount of a compound represented by the formula

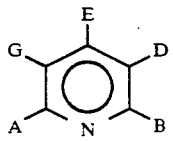

wherein:
one of A and B is selected from the group consisting of fluorinated methyl and chlorofluorinated methyl radicals, and the other is selected from the group consisting of fluorinated methyl, chlorofluorinated methyl and lower alkyl radicals;

E is selected from the group consisting of alkyl, alkenyl, cycloalkyl, cycloalkylalkyl, haloalkyl, and alkylthioalkyl radicals;

G is selected from the group consisting of hydroxycarbonyl, alkoxycarbonyl, haloalkoxycarbonyl, alkylthiocarbonyl, alkenyloxycarbonyl, alkynyloxycarbonyl, cyano, pyridylthiocarbonyl, aminocarbonyl, monoalkylsubstituted aminocarbonyl, and dialkylsubstituted aminocarbonyl, or is the same as D; and D is —NHR in which R is selected from the group consisting of 3-halopropylcarbonyl, 4-halobutylcarbonyl, and 2-haloethoxycarbonyl groups, optionally substituted with one or more groups selected from alkyl, fluoro, chloro, bromo, iodo, alkylidene, alkoxy, alkylthio, and haloalkyl radicals.

10. A method according to claim 9 wherein one of A and B is trifluoromethyl and the other is difluoromethyl.

11. A method according to claim 10 wherein E is selected from the group consisting of 2-methylpropyl, cyclobutyl, and cyclopropylmethyl.

12. A method according to claim 11 wherein R is 3-halopropylcarbonyl, optionally substituted with methyl.

* * * * *